United States Patent
Bushman

(10) Patent No.: US 11,864,960 B2
(45) Date of Patent: Jan. 9, 2024

(54) VALVE FOR FLUID EJECTOR

(71) Applicant: Crosstex International, Inc., Hauppauge, NY (US)

(72) Inventor: Richard P. Bushman, Oakdale, MN (US)

(73) Assignee: Crosstex International, Inc., Hauppauge, NY (US)

( * ) Notice: Subject to any disclaimer, the term of this patent is extended or adjusted under 35 U.S.C. 154(b) by 1059 days.

(21) Appl. No.: 16/321,594

(22) PCT Filed: Aug. 16, 2017

(86) PCT No.: PCT/US2017/047138
§ 371 (c)(1),
(2) Date: Jan. 29, 2019

(87) PCT Pub. No.: WO2018/035219
PCT Pub. Date: Feb. 22, 2018

(65) Prior Publication Data
US 2020/0397532 A1    Dec. 24, 2020

Related U.S. Application Data

(60) Provisional application No. 62/375,819, filed on Aug. 16, 2016.

(51) Int. Cl.
*A61C 1/00*    (2006.01)
*A61C 17/12*    (2006.01)
(Continued)

(52) U.S. Cl.
CPC .......... *A61C 1/0061* (2013.01); *A61C 17/13* (2019.05); *F16K 15/1848* (2021.08);
(Continued)

(58) Field of Classification Search
CPC ....... A61C 1/0061; A61C 17/08; A61C 17/13; A61M 39/22; A61M 2039/229;
(Continued)

(56) References Cited

U.S. PATENT DOCUMENTS 3,329,164 A    7/1967    Symonds et al.
3,363,650 A    1/1968    Scaramucci
(Continued)

FOREIGN PATENT DOCUMENTS

EP    1063948    1/2001

OTHER PUBLICATIONS

International Search Report and Written Opinion of the International Searching Authority dated Oct. 30, 2017 of International PCT Application No. PCT/US2017/047138 filed Aug. 16, 2017.
(Continued)

*Primary Examiner* — Kenneth Rinehart
*Assistant Examiner* — Jonathan J Waddy

(57) ABSTRACT

A valve assembly for a dental suction system. The valve assembly includes a valve body having an inlet, an outlet and a fluid flow path extending between the inlet and the outlet. The valve assembly also includes a valve plug positioned at least partially within the valve body and including a through-passage. The valve plug is rotatable relative to the valve body to selectively alter a flow of fluid along the fluid flow path. The fluid flow path exhibits a varied cross-sectional area along a length of the fluid flow path.

19 Claims, 14 Drawing Sheets

(51) Int. Cl.
   *F16K 15/18*   (2006.01)
   *A61M 39/22*   (2006.01)
   *A61M 39/24*   (2006.01)

(52) U.S. Cl.
   CPC ....... *A61M 39/22* (2013.01); *A61M 2039/229* (2013.01); *A61M 2039/246* (2013.01)

(58) Field of Classification Search
   CPC .............. A61M 2039/246; F16K 15/18; F16K 15/184; F16K 15/1848
   USPC ......................................................... 137/630
   See application file for complete search history.

(56) References Cited

U.S. PATENT DOCUMENTS

| | | | |
|---|---|---|---|
| 3,474,818 A | | 10/1969 | Hartman |
| 3,491,796 A | * | 1/1970 | Scaramucci .......... F16K 5/0605 251/315.13 |
| 3,846,885 A | * | 11/1974 | Perry .................... F16K 5/0207 29/434 |
| 4,846,221 A | * | 7/1989 | Kanemaru ............. F16K 5/0605 251/288 |
| 4,966,551 A | * | 10/1990 | Betush ................... A61C 17/08 604/32 |
| 5,181,539 A | * | 1/1993 | Yokoyama ................ F16K 5/06 251/315.04 |
| 5,514,089 A | | 5/1996 | Walbrink et al. |
| 5,725,374 A | * | 3/1998 | Young ...................... A61C 1/18 433/95 |
| 6,203,321 B1 | | 3/2001 | Helmer et al. |
| 8,256,464 B2 | | 9/2012 | Bushman et al. |
| 2003/0219696 A1 | * | 11/2003 | Moreland .............. A61C 17/08 433/91 |
| 2006/0180214 A1 | * | 8/2006 | Arentsen ............... F16K 27/067 137/613 |
| 2008/0289696 A1 | | 11/2008 | Bushman |
| 2009/0065067 A1 | * | 3/2009 | Bushman ............... A61C 17/13 137/217 |
| 2012/0193563 A1 | * | 8/2012 | Croci .................. F16K 15/1848 251/231 |
| 2016/0138723 A1 | * | 5/2016 | Al-Amri ............. F16K 15/1848 137/15.22 |
| 2017/0119497 A1 | * | 5/2017 | Thomas ................ F16K 5/0407 |
| 2018/0221839 A1 | * | 8/2018 | Aselton, II ........... B01F 35/714 |

OTHER PUBLICATIONS

Extended European Search Report dated Feb. 17, 2020, of related European Application No. 17842052.7 filed Aug. 16, 2018.
International Preliminary Report on Patentabiiity issued in PCT/US2017/047138, dated Feb. 28, 2019.

* cited by examiner

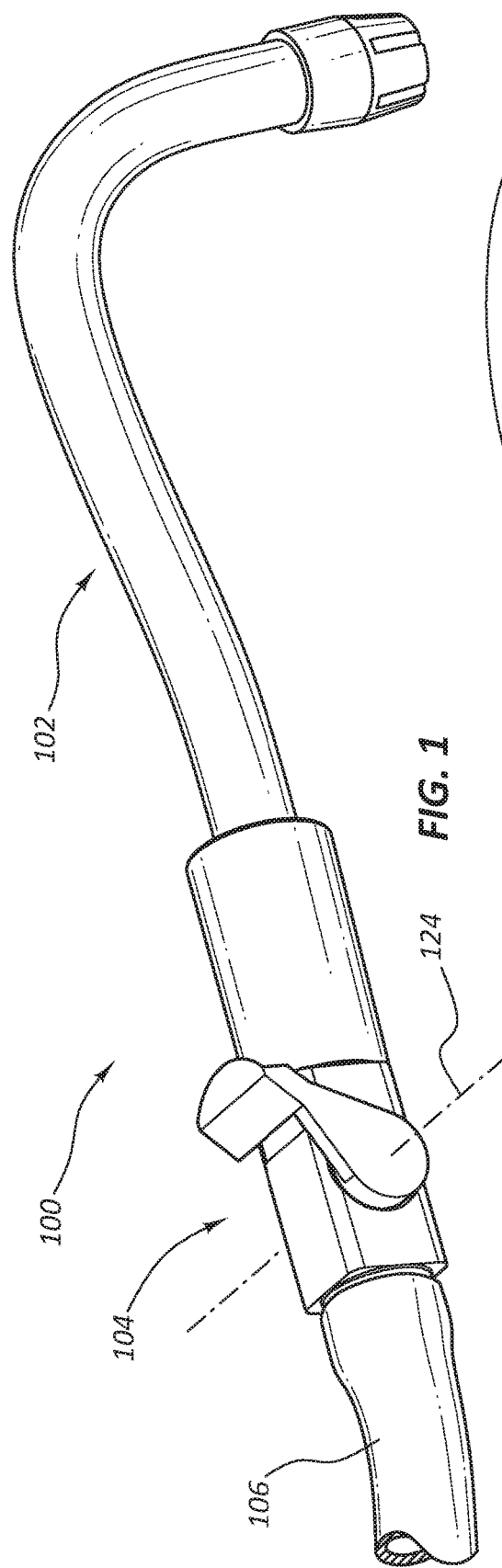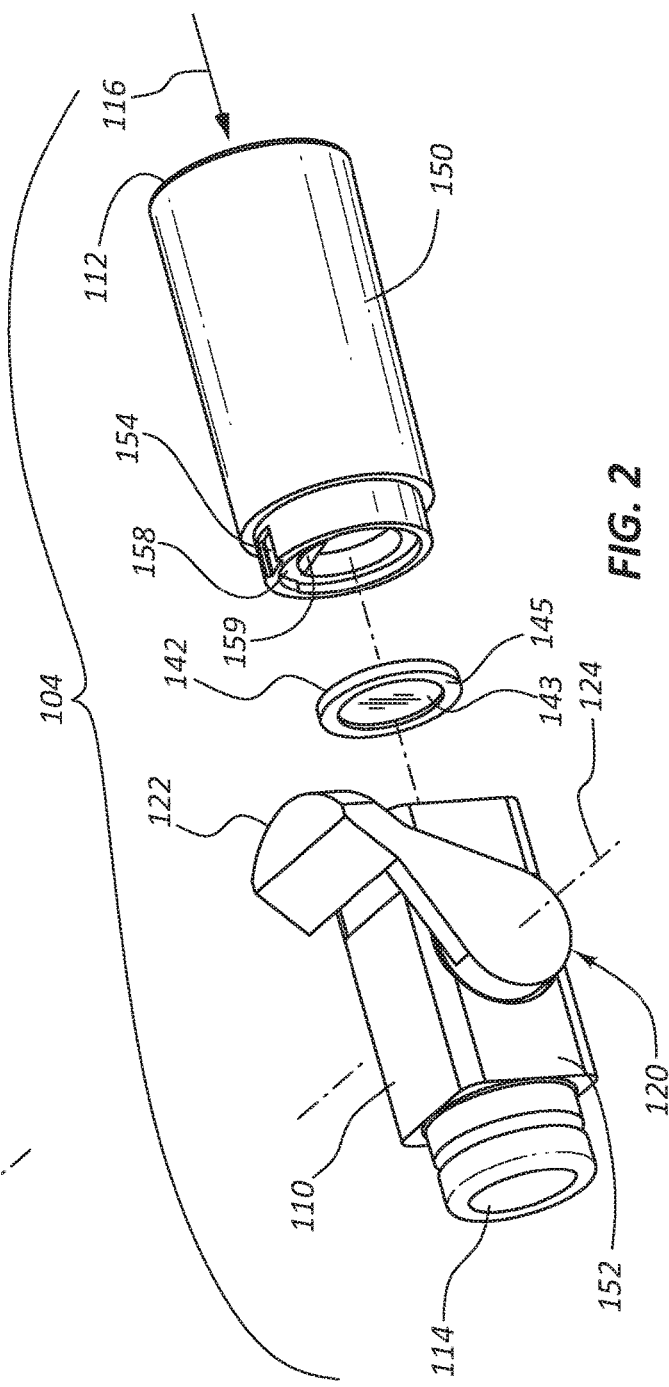

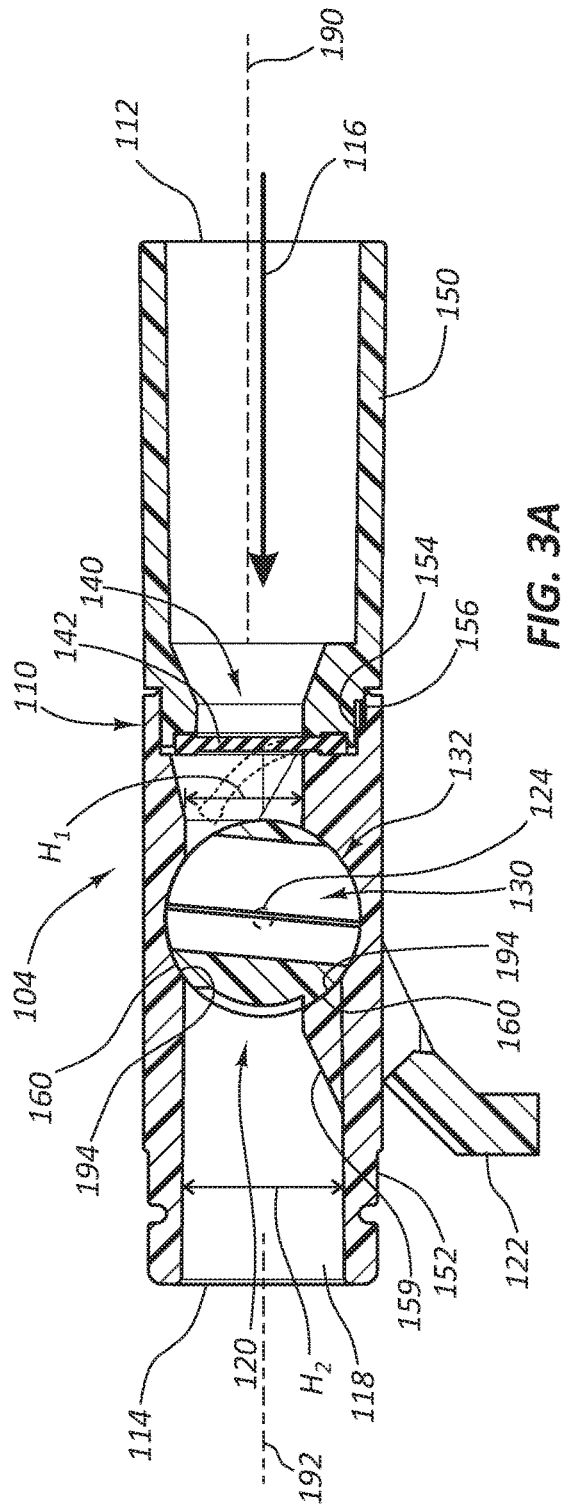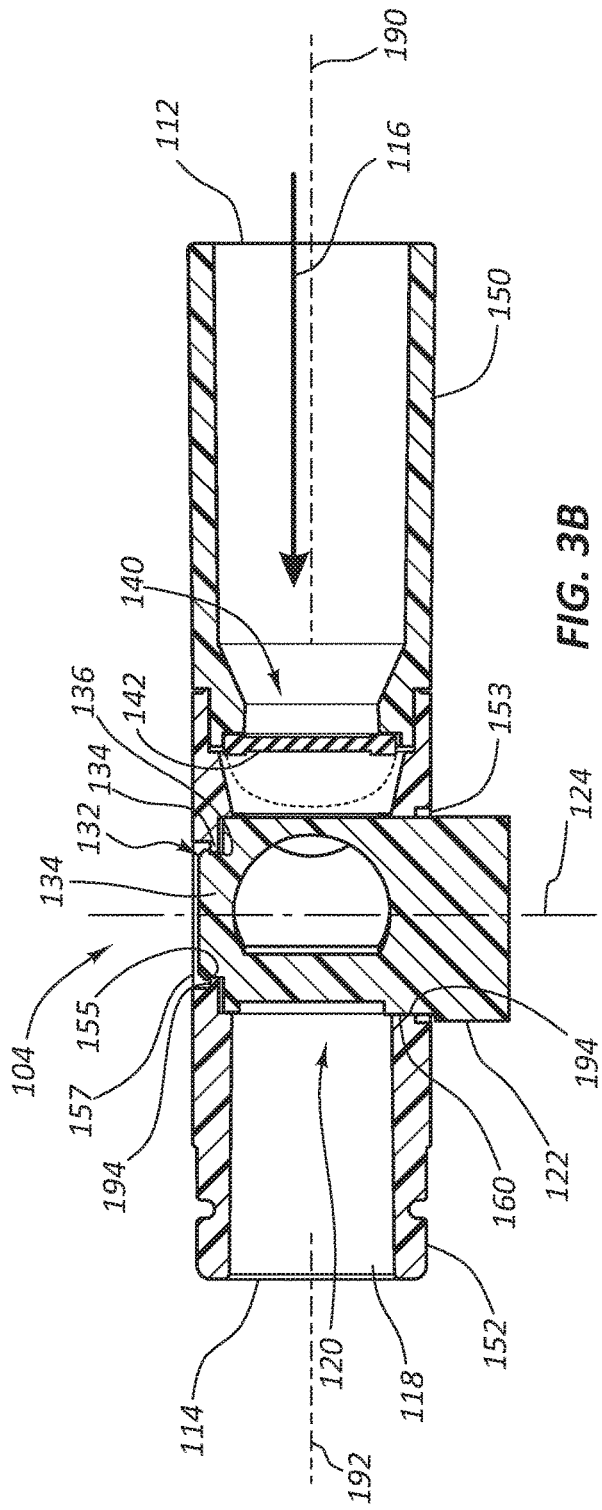

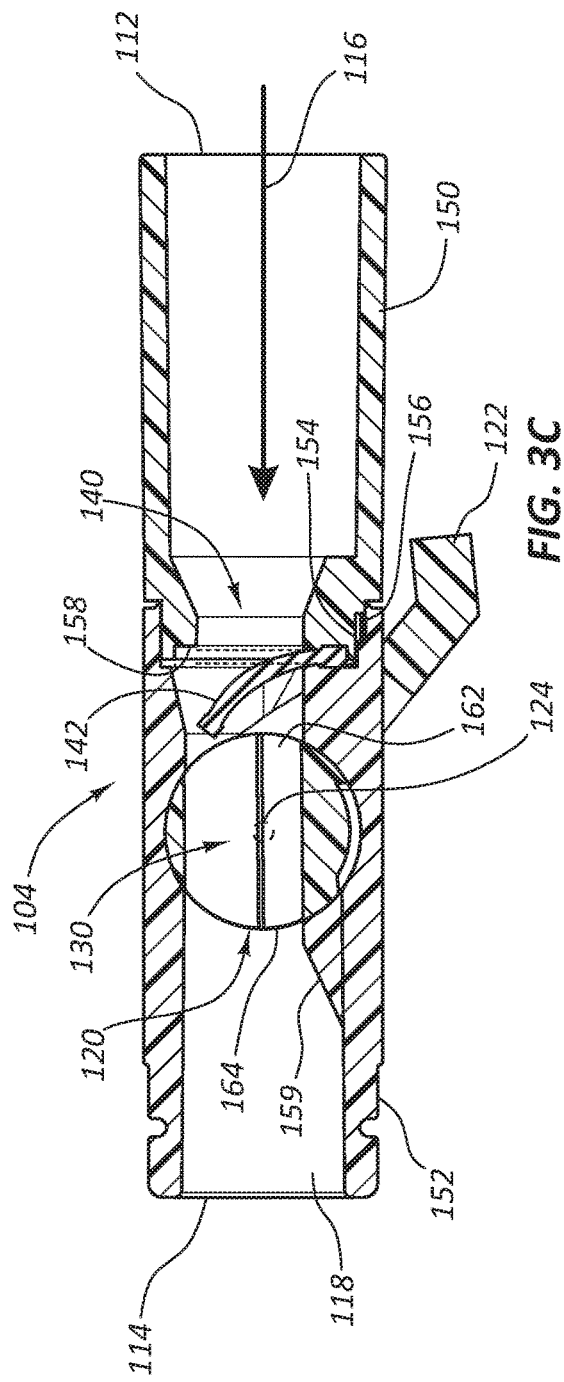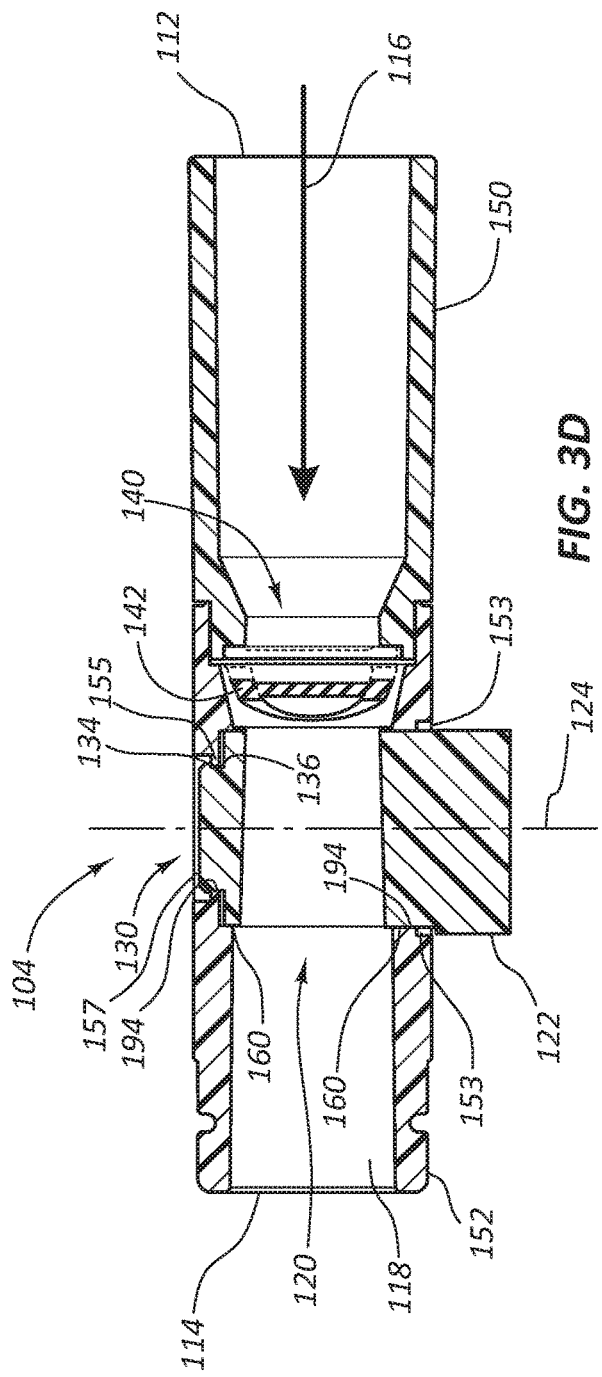
FIG. 3C
FIG. 3D

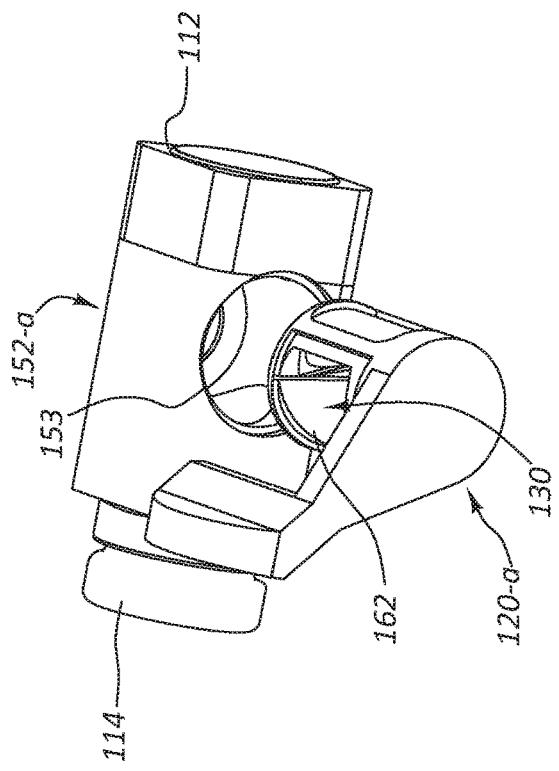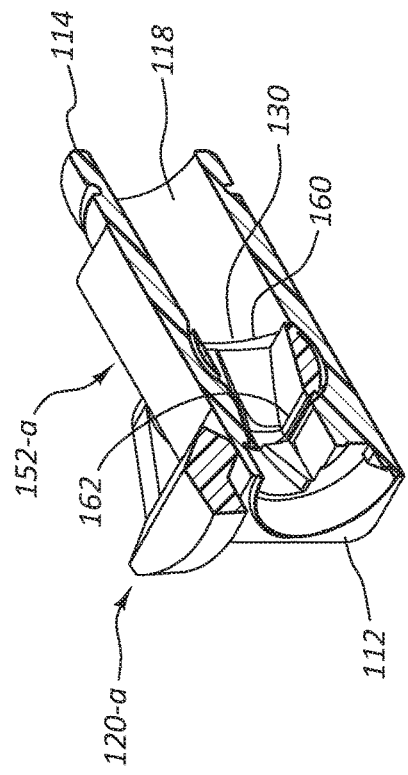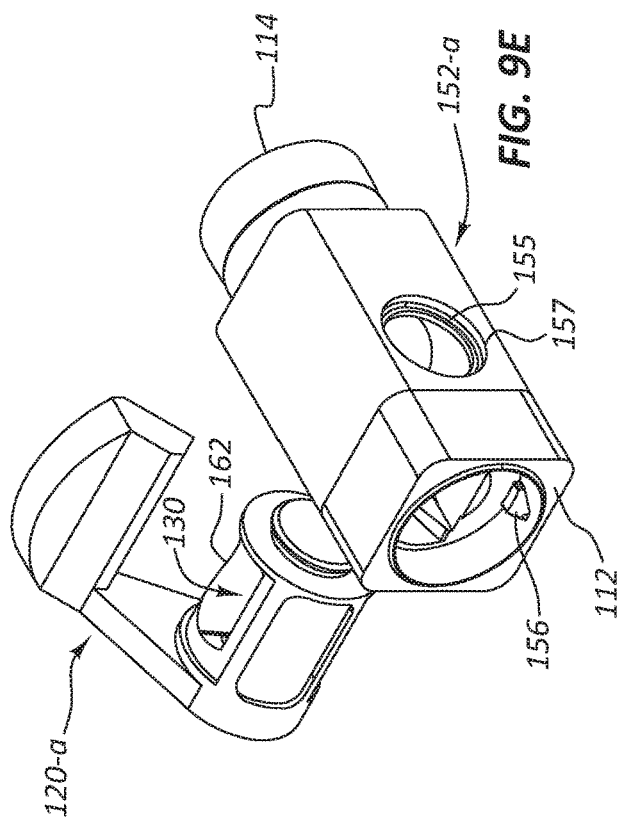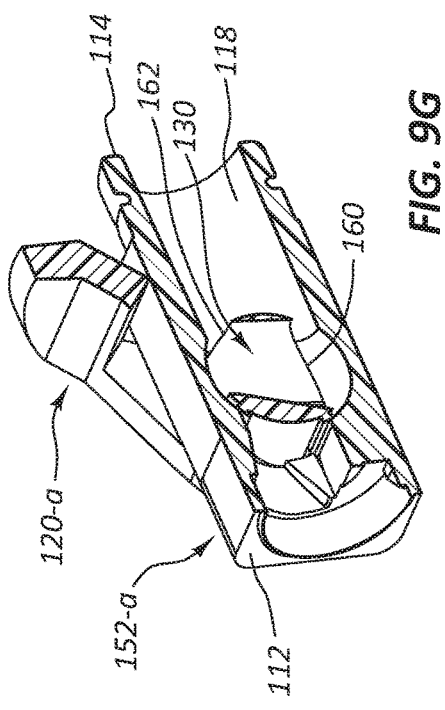
FIG. 9E
FIG. 9F
FIG. 9G
FIG. 9H

VALVE FOR FLUID EJECTOR

CROSS-REFERENCE TO RELATED APPLICATIONS

This application claims priority to U.S. Provisional Application No. 62/375,819 filed Aug. 16, 2016, and titled "Valve for Fluid Injector," the disclosure of which is hereby incorporated in its entirety by this reference.

TECHNICAL FIELD

The present disclosure generally relates to suctioning devices, and more particularly to valves associated with medical and dental suctioning devices.

BACKGROUND

Cross-contamination between patients, for example, dental patients, can occur when suctioning devices attached to vacuum lines are used to remove various bodily and/or externally introduced fluids. Although the disposable distal ends of these devices typically are changed between patients, the vacuum lines employed, along with various valves, typically are not changed. Saliva, blood and other contaminants pass from the distal end into the vacuum line, where they can remain until arrival of the next patient. When a new distal end is inserted onto the vacuum line for a new patient, contaminants from the previous patient can backflow from the vacuum line into the distal end and enter the patient's mouth, for example. Clearly, it is desirable to avoid such a situation.

Some suction devices may include suction lines having vacuum-release apertures through a tubular sidewall of a saliva ejector tip. If a patient closes his or her lips around the tip, the vacuum-release aperture is said to prevent creation of a temporary high vacuum in the patient's mouth; the aperture also likely prevents stoppage of air and/or fluid, at least between the aperture and the rest of the system. Other types of suction devices rely on a "tortuous path" within the device to substantially prevent backflow of bacteria.

However, due to various flow dynamics, including boundary layers formed around an internal circumference of many currently used suctioning devices, it is possible for a "biofilm" to be created along internal surfaces of the suction device, allowing saliva, blood and other contaminants to flow by gravity, for example, from a main vacuum system, through saliva ejector assemblies and into the mouths of patients.

Additionally, in many practices, the on/off valve of a suction device is "permanent" in that it is not conventionally replaced after use on a single patient. Rather, the same on/off valve is used with multiple patients creating the same concerns as outlined above with regard to contaminants flowing by gravity through a system and, eventually, into the mouths of patients.

As such, there is a continuing desire in the industry to provide valves and suction devices that minimize, if not eliminate, the potential exposure of patients to contaminants.

DISCLOSURE OF THE INVENTION

One aspect of the present disclosure relates to a valve assembly for a dental suction system. The valve assembly includes a valve body having an inlet, an outlet and a fluid flow path extending between the inlet and the outlet. The valve assembly also includes a valve plug positioned at least partially within the valve body and including a through-passage. The valve plug is rotatable relative to the valve body to selectively alter a flow of fluid along the fluid flow path. The fluid flow path exhibits a varied cross-sectional area along a length of the fluid flow path.

The valve assembly may also provide, when the through-passage is aligned with the fluid flow path to permit fluid flow through the valve body, the fluid flow path having a first portion having a first centerline and a second portion having a second centerline, wherein the first centerline is offset from the second centerline. The through-passage may include a first opening on a first side of the valve plug, a second opening on a second side of the valve plug, and a ramped surface extending at least partially between the first opening and the second opening. The first opening may have a semicircular geometry, and the second opening may have a semicircular geometry. The valve plug may form a seal with the valve body along a proximal side of the valve plug when the valve plug is in a closed position. The valve assembly may include at least one backflow prevention device disposed in the fluid flow path. The at least one backflow prevention device may be positioned between the valve plug and the inlet of the valve body. The at least one backflow prevention device may be positioned between the valve plug and the outlet of the valve body. The at least one backflow prevention device may include a flexible and resilient material, and be movable relative to the valve body to control fluid flow through the fluid flow path independent of operation of the valve plug.

Another aspect of the present disclosure relates to a valve assembly for a dental suction system. The valve assembly includes a valve body, a valve plug, and a backflow prevention device. The valve body has an inlet, an outlet and a fluid flow path extending between the inlet and the outlet. The valve plug is positioned at least partially within the valve body and includes a through-passage. The valve body is displaceable relative to the valve body to selectively alter a flow of fluid along the fluid flow path. The backflow prevention device is disposed in the fluid flow path between the valve plug and the inlet of the valve body or between the valve plug and the outlet of the valve body. The backflow prevention device is movable between open and closed positions to control fluid flow through the fluid flow path independent of operation of the valve plug.

The backflow prevention device may include a resilient, flexible member having a peripheral portion fixed relative to the valve body. The fluid flow path may be configured such that the fluid flow path includes a first portion having a first centerline distal of the valve plug and a second portion having a second centerline as proximal of the valve plug, wherein the first centerline is offset from the second centerline. The valve plug may be rotatable between open and closed positions. The valve plug may sealingly engage the valve body when the valve plug is in a closed position to block fluid flow through the fluid flow path.

A further aspect of the present disclosure relates to a valve assembly for a dental suction system. The valve assembly includes first and second valve bodies, a backflow prevention device, and a valve plug. The first valve body includes a first inlet, a first outlet, and a first fluid flow path extending between the first inlet and the first outlet. The second valve body includes a second inlet, a second outlet, and a second fluid flow path extending between the second inlet and the second outlet. The backflow prevention device is captured between the first and second valve bodies, and is movable to control fluid flow along at least one of the first and second fluid flow paths. The valve plug is positioned at least partially within the first valve body and includes a throughpassage. The valve body is displaceable relative to the valve body to selectively alter a flow of fluid along at least one of the first and second fluid flow paths.

The first fluid flow path may include a first portion having a first centerline distal of the valve plug and the second fluid flow path may include a second portion having a second centerline proximal of the valve plug, wherein the first centerline is offset from the second centerline. The backflow prevention device may be positioned between the valve plug and the first inlet. The backflow prevention device may be positioned between the valve plug and the first outlet. At least one of the first and second valve bodies may include an alignment feature configured to align the first valve body relative to the second valve body in a predetermined rotated position. The valve plug may form a seal with the second valve body along a proximal side of the valve plug when the valve plug is in a closed position.

The above summary is not intended to describe each disclosed embodiment or every implementation of the inventive aspects disclosed herein. Figures in the detailed description that follow more particularly describe features that are examples of how certain inventive aspects may be practiced. While certain embodiments are illustrated and described, it will be appreciated that disclosure is not limited to such embodiments.

BRIEF DESCRIPTION OF THE DRAWINGS

The foregoing and other advantages of the invention will become apparent upon reading the following detailed description and upon reference to the drawings in which:

FIG. 1 is a perspective view of a suction assembly according to an embodiment of the present disclosure;

FIG. 2 is an exploded perspective view of a valve assembly according to the present disclosure;

FIG. 3A is a cross-sectional view of the valve assembly shown in FIG. 2 with the valve in a closed position;

FIG. 3B is another cross-sectional view of the valve assembly shown in FIG. 3A;

FIG. 3C is a cross-sectional view of the valve assembly shown in FIG. 2 with the valve in an open position;

FIG. 3D is another cross-sectional view of the valve assembly shown in FIG. 3C;

FIGS. 9E and 9F are exploded perspective views of the portion of a valve assembly shown in FIGS. 9A and 9B;

FIGS. 9G and 9H are cross-sectional perspective views of the portion of a valve assembly shown in FIGS. 9A and 9B with the valve in closed and open positions, respectively;

BEST MODE(S) FOR CARRYING OUT THE INVENTION

Figure 4:
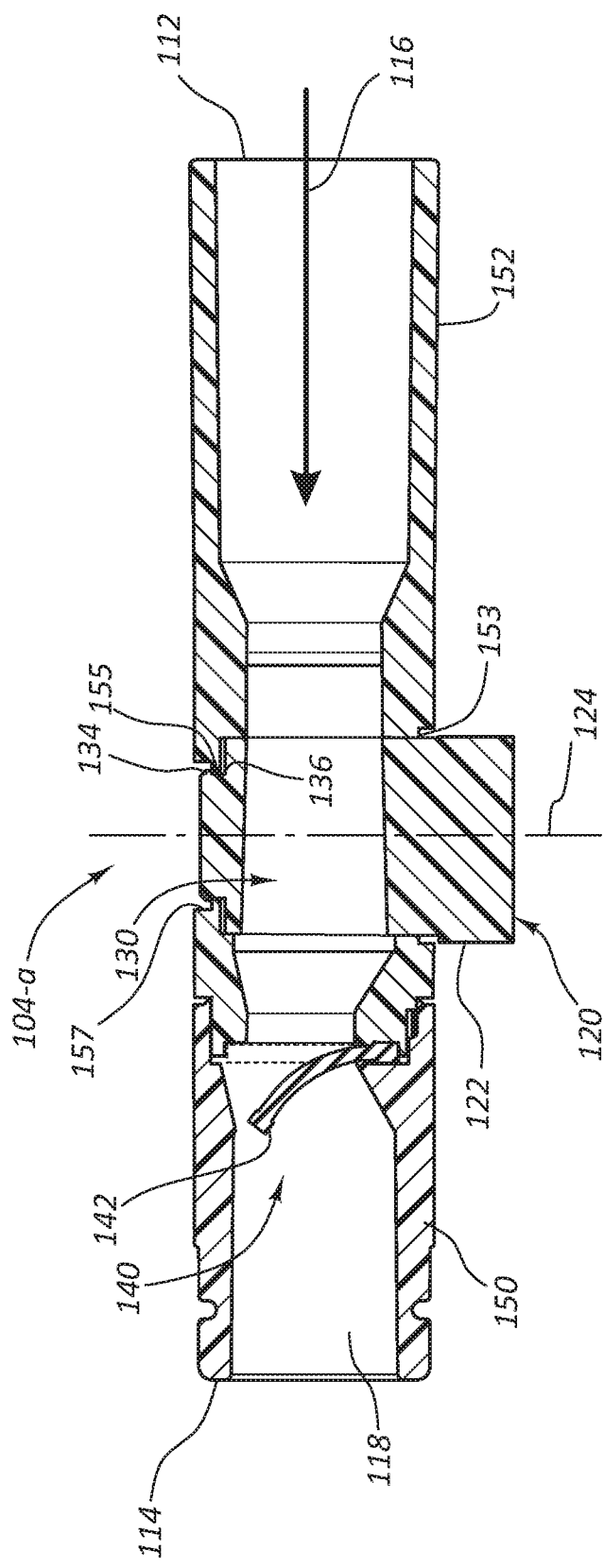
FIG. 4 is a cross-sectional view of another valve assembly embodiment in accordance with the present disclosure.

Various embodiments will be described in detail with reference to the drawings, wherein like reference numerals represent like parts and assemblies throughout the several views. Reference to various embodiments does not limit the scope of the claims attached hereto. Additionally, any examples set forth in this specification are not intended to be limiting and merely set forth some of the many possible embodiments for the appended claims.

The following discussion is intended to provide a brief, general description of a suitable environment in which the invention may be implemented. Although not required, the invention will be described in the general context of vacuum suction devices, for example, a dental saliva ejector device. The structure, creation, and use of some example dental fluid ejector devices and various components or subassemblies of components of such fluid ejectors are described hereinafter.

The example embodiments disclosed herein have wide application to a number of medical procedures and environments. Suction is often used in dental applications, as described above. Suctioning devices are also typically used to drain fluid and remove blood from many surgical environments, aid in respiration, and aid in a number of other medical and surgical procedures. Additionally, suctioning devices in which cross-contamination is undesirable are used in non-medical and non-surgical environments, such as in some types of liquid soap dispensers where preventing backflow of a fluid is required, and in the food service industry where various ingredients or food products must remain separated. Therefore, while most of the embodiments described with reference to the attached figures are directed to dental devices and applications, many other applications and related embodiments are envisioned.

An example suction assembly 100 is shown in FIG. 1. The suction assembly 100 includes an ejector tube assembly 102, an ON/OFF valve assembly 104 and a vacuum hose 106. The vacuum hose may be coupled with a vacuum source (not shown) as will be appreciated by those of ordinary skill in the art. While not explicitly shown in FIG. 1, the suction assembly 100 may include other components including, for example, and a cover member extending over the ON/OFF valve assembly 104 and a portion of the vacuum hose 106. Additionally, in some embodiments, a backflow prevention assembly may be coupled, for example, between the ON/OFF valve assembly 104 and the ejector tube assembly 102, or between the ON/OFF valve assembly 104 and the vacuum hose 106. A backflow prevention assembly may be integrated into the ON/OFF valve assembly 104. Some non-limiting examples of backflow prevention assemblies are described in U.S. Pat. No. 8,714,200, issued May 6, 2014, to Bushman et al., and U.S. Pat. No. 6,203,321, issued Mar. 20, 2001, to Helmer et al., the disclosures of each of which are incorporated herein in their entireties by this reference. In other embodiments, such as shall be described in further detail below, a backflow prevention structure or assembly may be incorporated into the ON/OFF valve assembly 104 in a variety of ways and/or locations, as will be described herein.

FIG. 2 is a perspective view of an ON/OFF valve assembly 104 which may be used in a suction assembly such as the suction assembly 100 depicted in FIG. 1, for example. The ON/OFF valve assembly 104 includes a housing or body assembly 110 having a distal end 112 (which may also be referred to as an inlet) configured for connection with an ejector tube 102, or other similar device, and a proximal end 114 (which may also be referred to as an outlet) configured for connection with a vacuum hose 106. As indicated by directional arrow 116, flow is intended to pass through the valve from the distal end 112 to the proximal end 114. The body assembly 110 includes a distal portion 150, which defines the distal end 112, and a proximal portion 152, which defines the proximal end 114. The distal and proximal portions 150, 152 may include alignment features to provide a predetermined rotational alignment of the portions 150, 152 when connected together. For example, the distal portion 150 may include an alignment groove (see FIGS. 2 and 5) that mates with an alignment protrusion 156 of the proximal portion 152 (see FIGS. 5 and 7).

The ON/OFF valve assembly 104 also includes a rotary valve plug 120 coupled with a lever 122. The valve plug 120 is at least partially disposed within the valve body 110 and is configured to rotate relative to the valve body 110 about an axis 124. Rotation of the valve plug 120 about the axis 124 may be accomplished by a user applying a force (e.g., with their thumb) to the lever 122. The plug includes an opening therethrough (as discussed in further detail below) such that when rotated to a first position (e.g., an "OFF" position), fluid flow from the distal end 112 to the proximal end 114 is interrupted, but when rotated to a second position (e.g., an "ON" position), fluid flow from the distal end 112 to the proximal end 114 is permitted.

Referring to both FIGS. 1 and 2, during use of the suction assembly 100, suction is applied by way of a vacuum source coupled with the vacuum hose 106. An operator actuates the valve plug 120, moving it from an OFF position to an ON position by way of the associated lever 122, and the end of the ejector tube assembly 102 is placed adjacent an area where fluid removal is required (e.g., in a patient's mouth to remove saliva). When suction is no longer required, the operator again actuates the valve plug 120, moving it from the ON position to the OFF position, and places the suction assembly 100 in a temporary holding location until suction is again needed for a given patient.

After the suction assembly 100 is finished being used for a given patient, the ejector tube assembly 102 and the ON/OFF valve assembly 104 may be removed from the vacuum hose and disposed of. A new ON/OFF valve assembly 104 and a new ejector tube assembly 102 may be coupled to the vacuum hose for use with each new patient. As will be described in further detail below, various components of the ON/OFF valve assembly 104 may be formed of relatively inexpensive materials (e.g., polymeric materials) and formed using relatively inexpensive manufacturing processes (e.g., molding) to provide inexpensive, disposable products in an effort to maintain the highest possible sterility in a dental or medical environment. In other embodiments, the ON/OFF valve assembly 104 may comprise different materials and/or different manufacturing processes to provide a more expensive, multi-use product that can be cleaned and reused.

Referring now to FIGS. 3A-3D, several cross-sectional views are shown of an ON/OFF valve assembly 104 according to an embodiment of the present disclosure, such as the embodiment shown in FIG. 2. As previously noted, the valve assembly 104 may include a valve body 110 having a distal end 112 and a proximal end 114. In some embodiments, the valve body may be a single, substantially homogenous structure. In other embodiments, the valve body 110 may be formed of multiple body portions 150, 152 such as seen in FIGS. 3A-3D. A valve plug 120 is at least partially disposed within the valve body 110 and configured to rotate about a defined axis 124. An opening or a through-passage 130 is formed in the valve plug such that when the valve plug 120 is in an "ON" position, the through-passage 130 is substantially aligned with a flow path 118 between the distal and proximal ends 112, 114 of the valve body 110 (as shown in FIGS. 3A-3B), enabling fluid flow through the valve assembly 104. When the valve body 110 is rotated to an "OFF" position, the through-passage 130 is placed at an angle relative to the flow path between the distal and proximal ends of the valve body 110 such that fluid flow is interrupted or inhibited (as shown in FIGS. 3C-3D).

Figure 7:
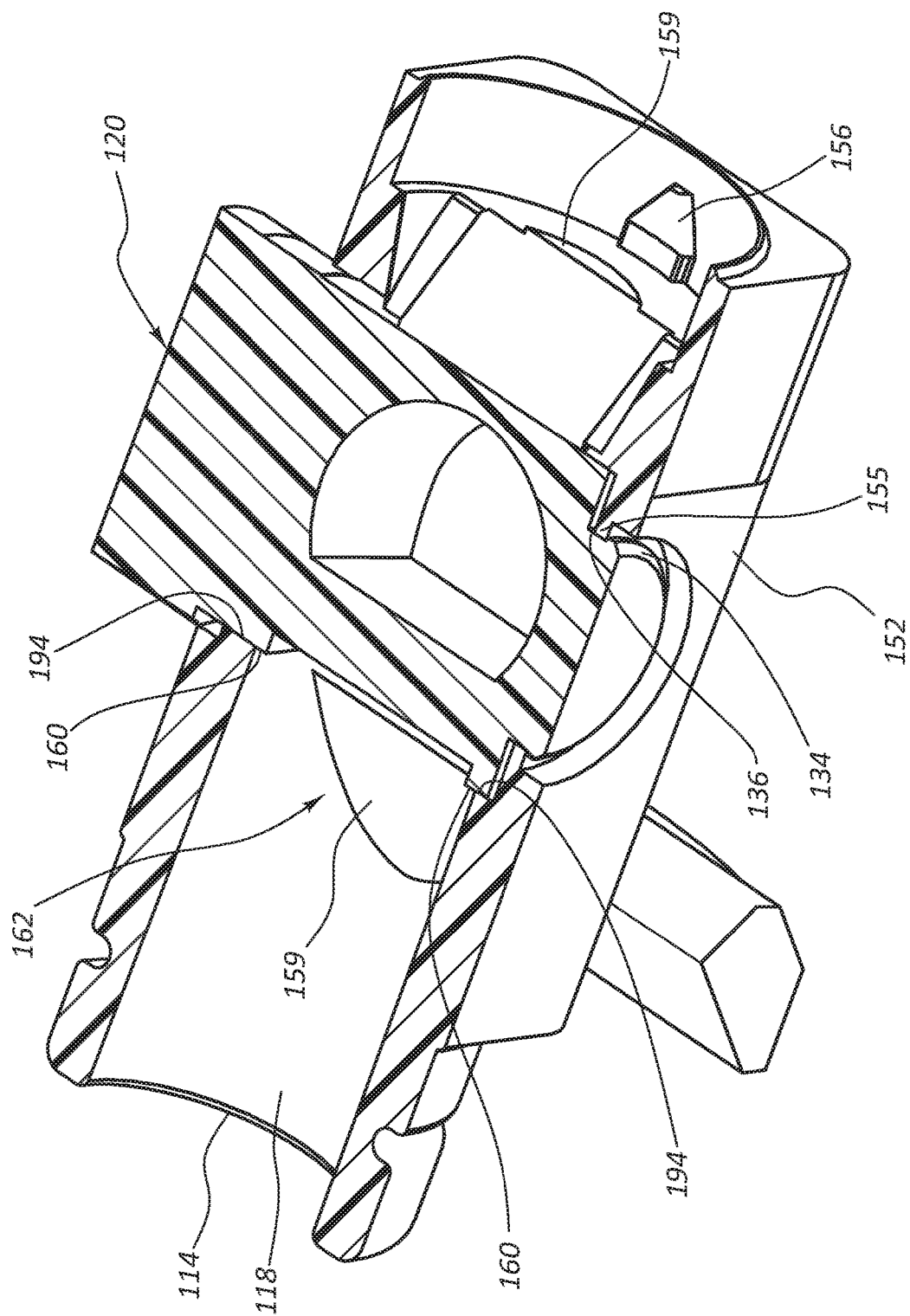
FIG. 7 is a cross-sectional perspective view of a portion of the valve assembly shown in FIG. 2.

The valve plug 120, while rotatable relative to the valve body 110, may be sealed relative to the valve body 110 so that fluid does not leak between the valve body 110 and the valve plug 120. For example, in one embodiment, the valve plug 120 may extend through an opening 132 formed in the valve body 110. A ridge or lip 134 and groove 136, which are formed on the valve plug 120 may cooperatively engage an aperture rim 155 formed in the valve body 110 at an outer valve aperture 157 to form a fluid-tight seal therebetween. A detailed view of the connection point between the valve body 110 and the valve plug 120 is shown in FIG. 7. The sealed connection point between the valve body 110 and the valve plug 120 may be located at a side of the valve body 110 opposite the side where the valve plug 120 is inserted into the opening 132 of the valve body 110, and opposite the side of the valve plug 120 where the lever 122 is connected. A inner valve aperture 153 is provided along that surface of body portion 152 where the valve plug 120 is inserted (see FIG. 3B).

In other embodiments, the lip/groove and rim arrangement may be reversed between the valve body 110 and the valve plug 120. In yet other embodiments, corresponding grooves may be formed in each of the valve body 110 and the valve plug 120, and an O-ring or other seal member may be disposed within the corresponding grooves to provide a desired seal therebetween. In yet further embodiments, depending on the level of suction being drawn through the valve assembly 104, an close interference fit between the valve body 110 and the valve plug 120 may be sufficient to provide a seal therebetween. In some embodiments, the connection provided between the valve body 110 and the valve plug 120 may be a snap-fit connection. The connection between the valve body 110 and the valve plug 120 may be a releasable connection to provide assembly and disassembly of the valve assembly 104 as desired. In other embodiments, the connection may be a permanent connection such that the damage to the valve assembly 104 would result from attempting to disconnect the valve plug 120 from the valve body 110.

The valve assembly 104 may also incorporate a backflow prevention device 140. The backflow prevention device 140 may operate as a check valve to help prevent fluids from draining or flowing in the direction toward the distal end 112 of the valve assembly 104 regardless of the operational position of the valve plug 120 (e.g., even if the valve plug 120 may be in an "OFF" position). The backflow prevention device 140 may prevent drainage or backflow of fluids in the event that vacuum is lost while the valve plug 120 is in the "ON" position.

In one embodiment, the backflow prevention device 140 may include a flexible and resilient member 142 having a first portion fixed relative to the valve body 110 and a second portion that is displaceable relative to the valve body 110. Thus, for example, when the valve plug is in the "ON" position and suction is applied through the valve assembly 104, the flexible nature of the member 142 enables a portion to be displaced relative to the valve body 110 (as shown in FIG. 3C) to enable flow in the direction indicated by arrow 116. However, the resilient nature of the member 142 causes it to automatically return to a "closed" state when suction is not being applied to the valve assembly 104 (and/or when the valve plug 120 is in the "OFF" position—see FIG. 3A). The member 142, therefore, acts as a check valve for the valve assembly 104. Such a backflow prevention device 140 may be constructed such as described in previously incorporated U.S. Pat. No. 8,714,200. Of course, other types of backflow prevention devices may be incorporated into valve assembly 104 if desired.

Figure 5:
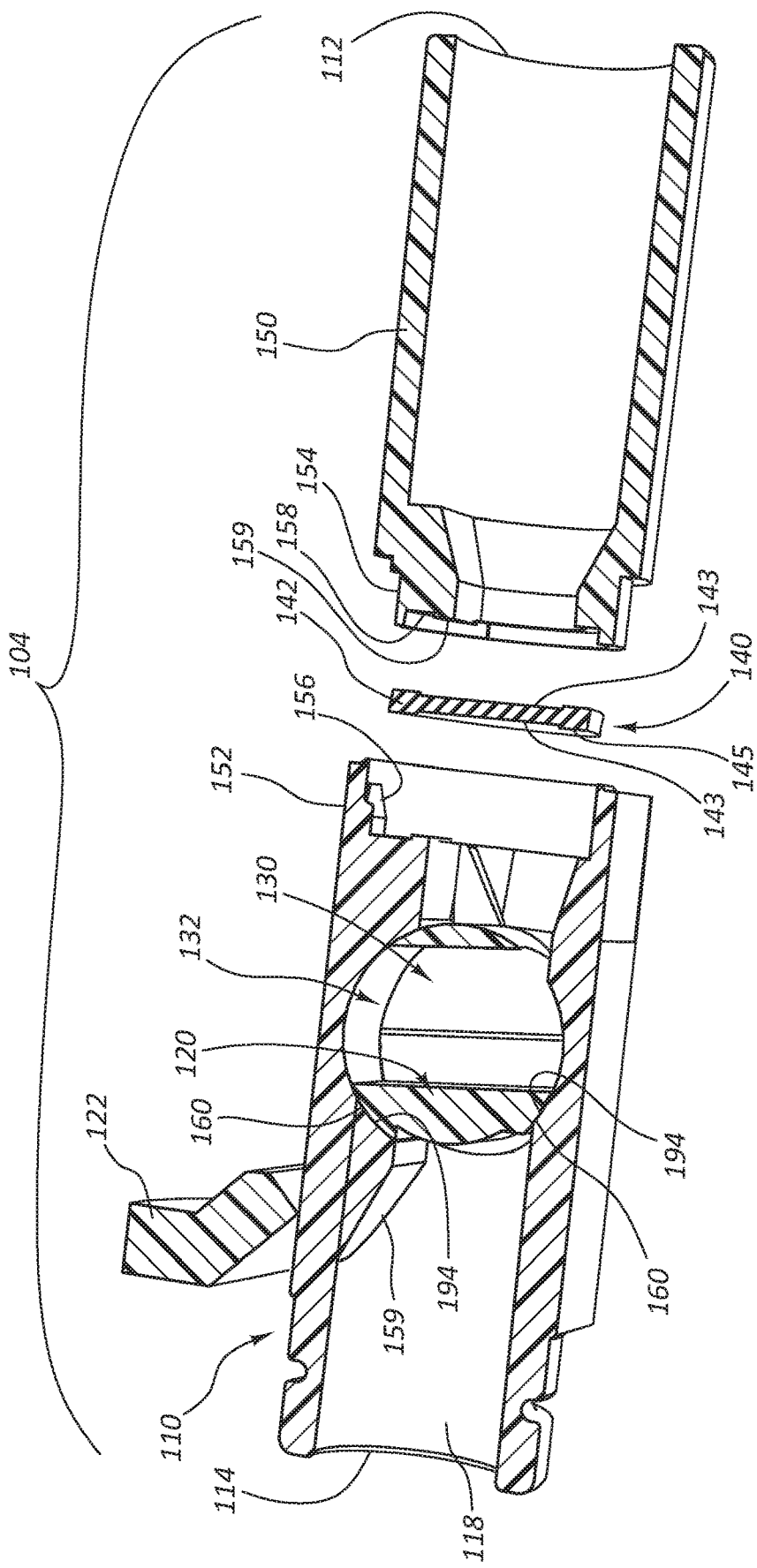
FIG. 5 is an exploded, cross-sectional perspective view of the valve assembly shown in FIG. 2.

The resilient member 142 of the backflow prevention device 140 may be captured between the distal and proximal portions 150, 152 of the body assembly 110. The resilient member 142 may be held at a location inside an outer periphery of the resilient member 142, such as radially in from an outer circumferential edge of the resilient member 142, as shown in at least FIGS. 3A and 3C. The resilient member 142 may be positioned within a valve seat 158 formed in at least one of the distal and proximal portion 150, 152 of the body assembly 110. FIGS. 3C and 5 shown an example valve seat 158 formed in the distal portion 152. The resilient member 142 may contact a surface of the valve seat 158 to form a fluid-tight seal that prevents backflow of fluids when the resilient member 142 is in the closed position shown in, for example, FIGS. 3A and 6.

At least one of the distal and proximal portions 150, 152 may include one or more valve retention features 159 to assist with securing the resilient member 142 in place. FIG. 5 shows separate valve retention features 159 positioned on each of the distal and proximal portions 150, 152. FIGS. 2 and 5 show a valve retention feature 143 on the distal portion 150. FIGS. 5, 7 and 9A-9B show a valve retention feature 159 on the proximal portion 152. The valve retention features 159 may be sized and arranged to interface with a recess 143 of the resilient member 142. The recess 143 may be positioned radially inward from a rim 145 of the resilient member 142 (see FIGS. 2, 5 and 6).

In the embodiment shown in FIGS. 3A-3D, the backflow prevention device 140 is placed upstream of the valve plug 120 (e.g., between the distal end 112 of the housing and the valve plug 120 in the specific embodiment shown in FIGS. 3A-3D). Such an embodiment may provide the advantage of contaminants that may have reached the valve plug 120 (e.g., from the vacuum hose 106) being blocked from possibly draining beyond the backflow prevention valve in certain situations. FIG. 4 shows a valve assembly 104-*a* having substantially similar components as the valve assembly 104 shown in FIGS. 3A-3D, except that the backflow prevention device 140 is positioned down-stream from the valve plug 120. Such an embodiment may provide the advantage of helping to prevent contamination from a vacuum hose ever reaching the valve plug 120 in certain circumstances. While not shown, in other embodiments, a valve assembly may include multiple backflow prevention devices including one or more positioned upstream of the valve plug 120 and one or more positioned downstream of the valve plug 120. In yet other embodiments, the valve assembly 104 may not include any backflow prevention devices.

FIG. 5 is an exploded cross-sectional view of the valve assembly 104 depicted in FIGS. 3A-3D, showing a two-piece valve body 110 (e.g., distal portion 150 and proximal portion 152) that may be used in conjunction with certain backflow prevention devices 140. Additionally, FIG. 5 shows the opening 132 through which a portion of the valve plug 120 extends (lever 122 of the valve plug 120 not shown in FIG. 5). In one embodiment, a backflow prevention member 142 may be positioned between the distal portion 150 and proximal portion 152 of the valve body 110, with a portion of the backflow prevention member's peripheral edge being clamped between the two portions 150, 152 such as described in previously incorporated U.S. Pat. No. 8,714,200.

Figure 6:
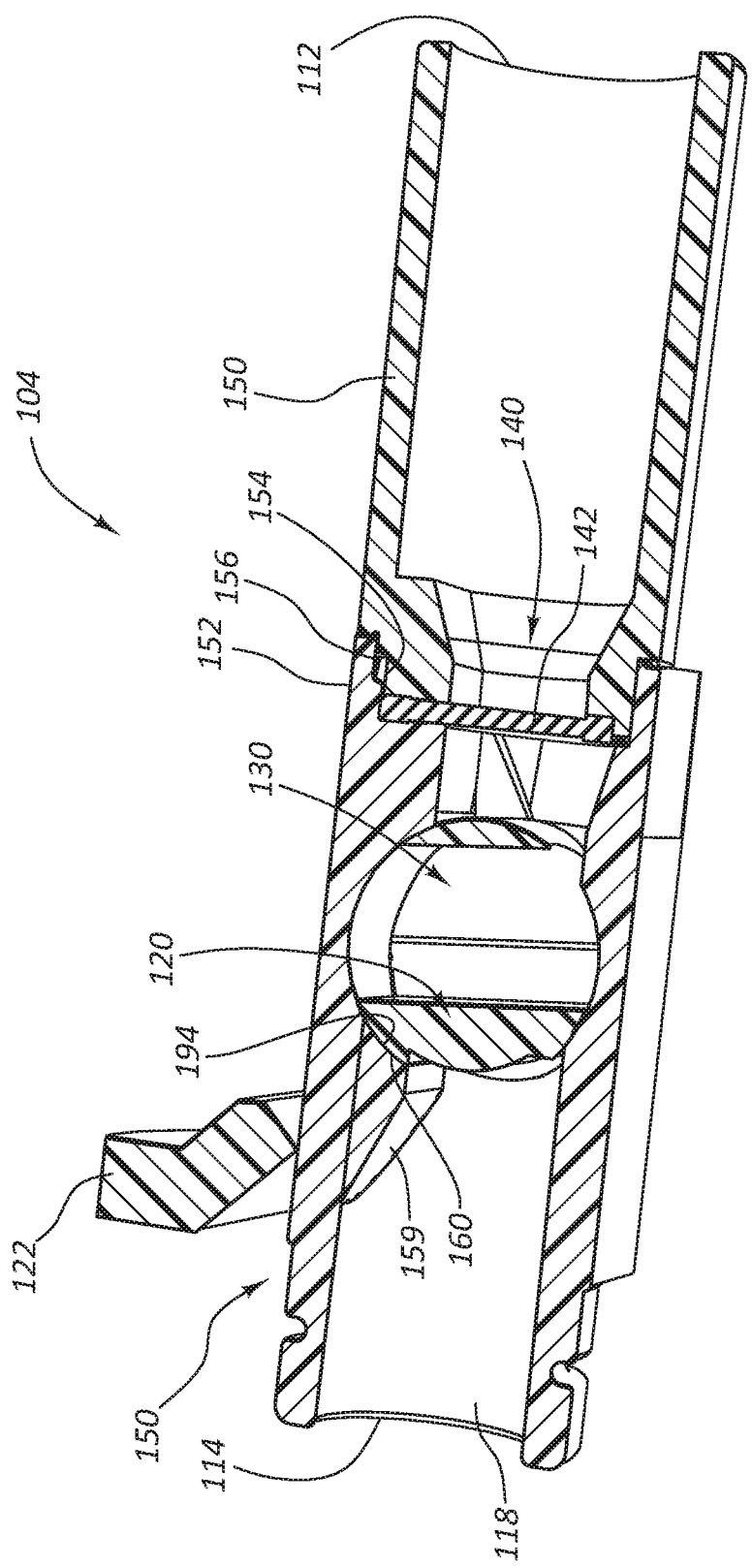
FIG. 6 is a cross-sectional perspective view of the valve assembly shown in FIG. 2.

Referring to FIGS. 6 and 7, cross-sectional views of an ON/OFF valve assembly 104 are shown (with certain portions removed in FIG. 7 for purposes of clarity). FIGS. 6 and 7 show the through-passage 130 of the valve plug 120 in further detail. While in some embodiments, the through-passage 130 may include a through-bore having a substantially constant cross section, the through-passage 130 depicted in FIGS. 6 and 7 includes a through-bore that may have a constant cross-sectional area along the intended path of fluid flow (as taken perpendicularly to the intended path of fluid flow). In other embodiments, the through-passage 130 may include a variable cross-section resulting from, for example, a ramp portion extending along at least a portion of the through-passage 130 such that an opening 162 on one side of the valve plug 120 exhibits a larger cross-sectional area than an opening 164 on the opposing side of the valve plug 120 (e.g., see embodiment shown in FIGS. 10A-11C).

In some embodiments, the flow path 118 through the body assembly 110 may have variable cross-sectional size along its length between the distal and proximal ends 112, 114. The flow path may include, for example, a ramp portion 159. The ramp portion 159 may be positioned at a proximal end of the valve plug 120 and provide a transition to an outlet opening 164 of the valve plug 120 (see FIG. 3C). Thus, in the embodiments depicted, the downstream outlet opening at proximal end 114 may exhibit a larger cross-sectional area than does other portions of the flow path 118, including a portion of the flow path defined by the valve plug 120 when in the "ON" position. Referring to FIG. 3A, a portion of the flow path 118 upstream of the valve plug 120 may have a height H1 (e.g., a diameter), and a portion of the flow path 118 downstream of the valve plug 120 may have a height H2, which is greater than the height H1. Such a configuration may provide various advantages including, for example, a shorter "throw" of the valve plug being required between the ON and OFF positions. In other words, the change in cross-sectional area along the length of the through-passage 130 may result in the valve plug 120 rotating through a smaller angle of rotation relative to the valve body 110 between the ON and the OFF positions.

Figure 8A:
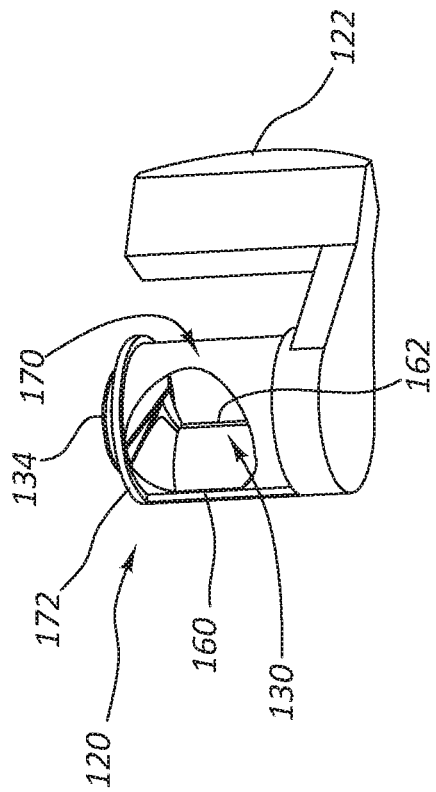
FIGS. 8A-8C are various views of a component of the valve assembly shown in FIG. 2.
Figure 8B:
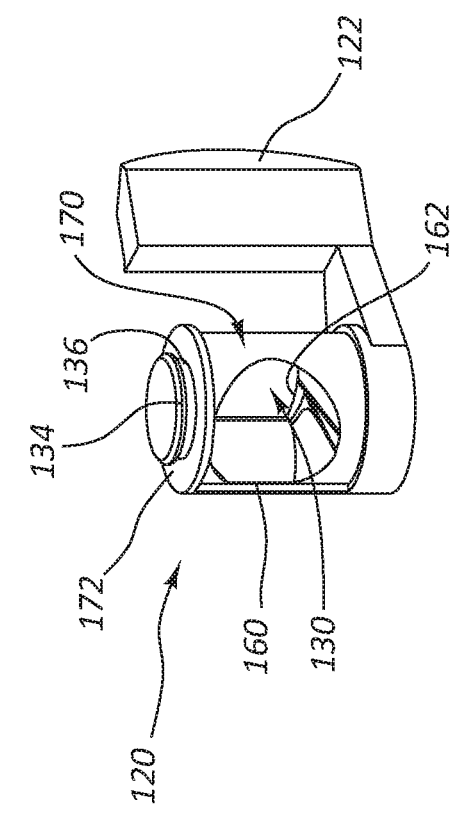
Figure 8C:
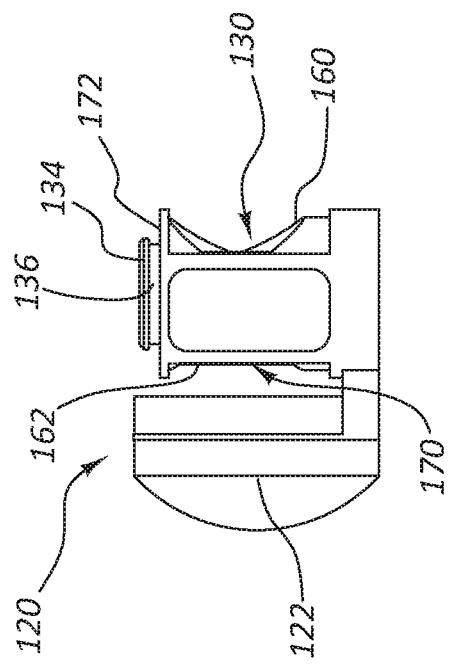
Figure 8D:
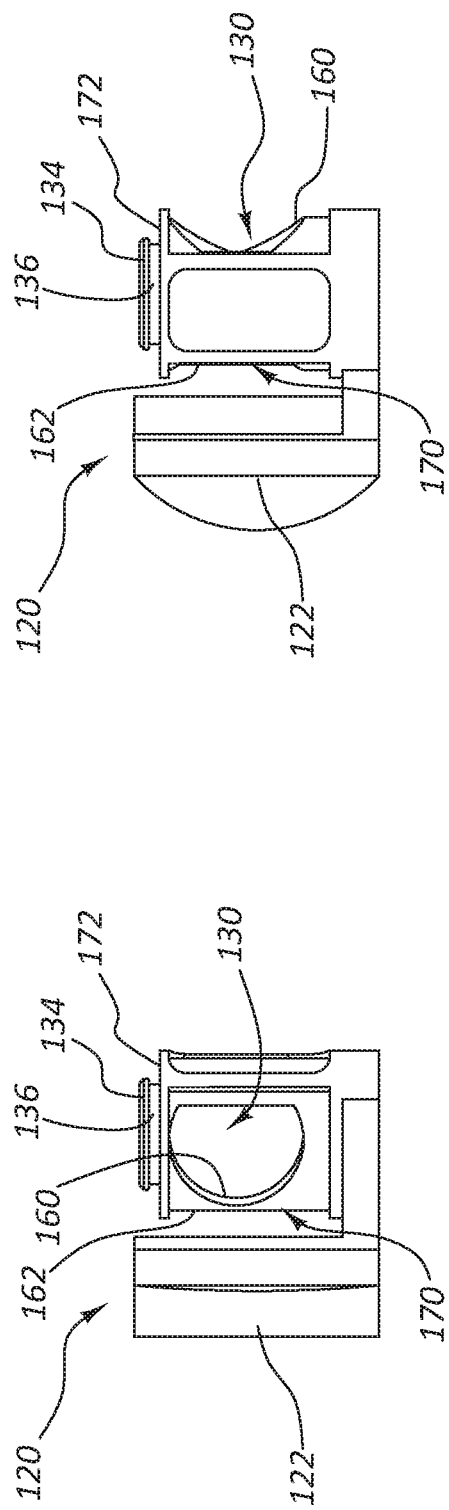

FIGS. 8A-8D include various views of a valve plug 120 according to an embodiment of the disclosure, including a through-passage 130 and openings 162, 164 (such as described above). In one particular embodiment, such as best seen in FIG. 8C, both the inlet opening 162 and the outlet opening 164 of the through-passage 130 may be semi-circular in geometry. However, other geometries are also contemplated and the examples shown in FIGS. 8A-8D are not to be considered limiting. It is also noted that the valve plug 120, as shown in FIGS. 8A-8D, may include a body portion 170 that is substantially cylindrical. However, the body portion 170 may exhibit other geometries including, for example, conical, frustoconical, spherical, semispherical, etc.

FIGS. 8A-8D also show the lip 134 formed on a portion of the valve plug 120 and circumscribing the perimeter of the body portion 170. A groove 136 may be formed adjacent to the lip 134 in certain embodiments. It is also noted that, in some embodiments, a second lip may be formed on the valve body such that at least one lip is positioned on opposite sides of the through-passage 130 in a spaced apart manner along the axis of rotation 124 (see FIG. 2) of the valve plug 120. In yet other embodiments, a single lip may be formed at a different location on the body portion 170 of the valve plug 120 (e.g., on the opposite side of the through passage than is shown in FIGS. 8A-8D along the axis of rotation 124). It is noted that the valve plug 120 is also depicted having a surface 172 formed on a peripheral surface at a location opposite the lever 122. In some embodiments, the surface 172 may engage an cooperative internal surface formed in the valve body 110 to help align the valve plug 120 within the valve body 110. In other embodiments, the valve plug 120 may include a radius, chamfer or other surface feature formed in or in place of the surface 172, or may simply include a direct angular transition from one surface to another without a transition of a chamfer or radius.

FIGS. 3A, 5 and 7 show the valve plug 120 rotated into a closed or "OFF" position. In the closed position, a rear sealing surface 160 of the valve plug 120 is arranged at a proximal or rear side of the valve plug 120 to contact a sealing surface 194 of the valve body portion 152 to form a seal therebetween. Positioning this sealing interface at a proximal or rear side (e.g., an "exit" side) of the valve plug 120 when the valve plug 120 is rotated into a closed position may provide advantages related to creating and maintaining the sealing when the valve plug 120 is in the closed or "OFF" position. One objective of the design shown in FIGS. 3A-3D is to seal against the exit side of the valve body rather than the inlet side (e.g., see embodiment shown in FIGS. 10A-11C). When sealing against the exit side via the interface between rear sealing surface 160 of the valve plug 120 and the sealing surface 194 of the valve body portion 152 as provided by the embodiment of FIGS. 3A-3D, the valve plug 120 only has to seal around the exit of the valve plug 120 and not also around the rotation axis on each side of the valve plug 120. In contrast, the embodiment of FIGS. 10A-11C, which provides a seal between the valve plug and the valve body at an entrance of the valve plug when the valve plug is rotated into a closed position, may also require sealing between the valve body and the valve plug along the rotation axis of the valve plug.

Figure 9B:
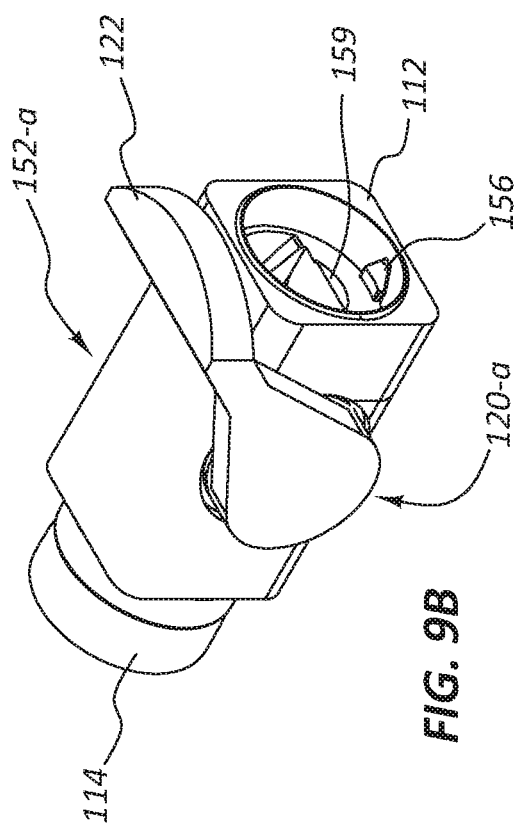
FIGS. 9A and 9B are perspective views of a portion of a valve assembly in an open position in accordance with the present disclosure.
Figure 9D:
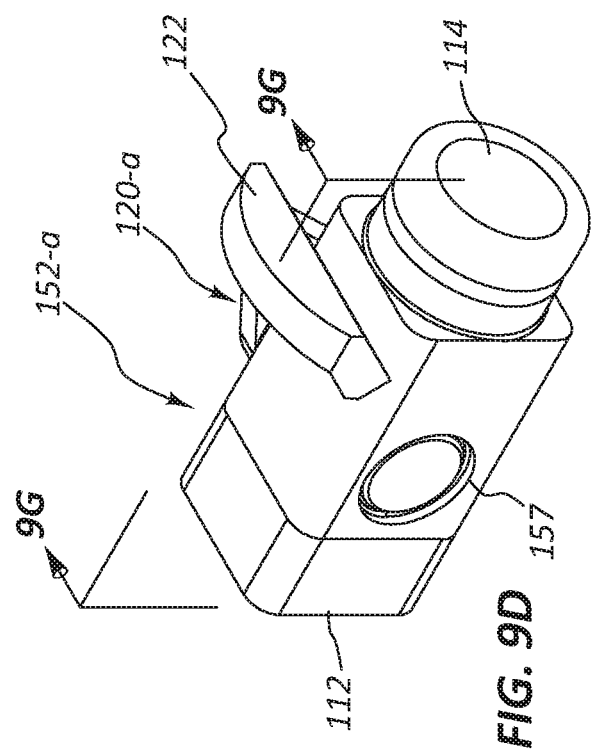
FIGS. 9C and 9D are perspective views of the portion of a valve assembly shown in FIGS. 9A and 9B with the valve in a closed position.
Figure 9A:
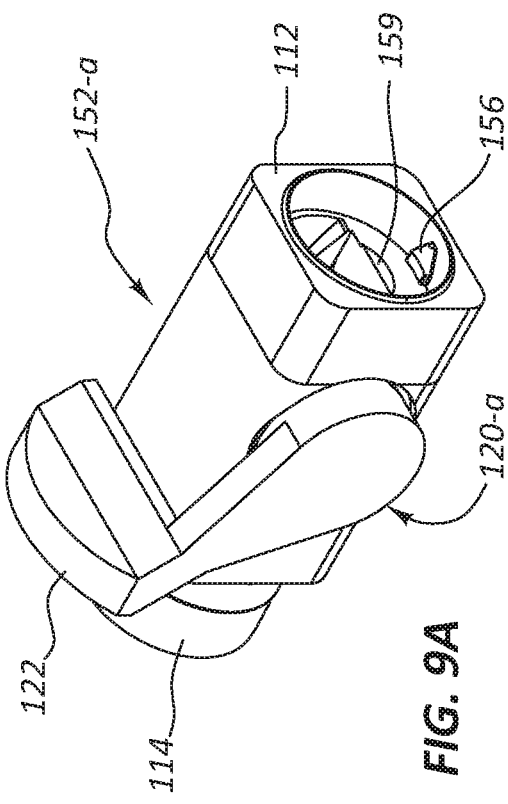
Figure 9C:
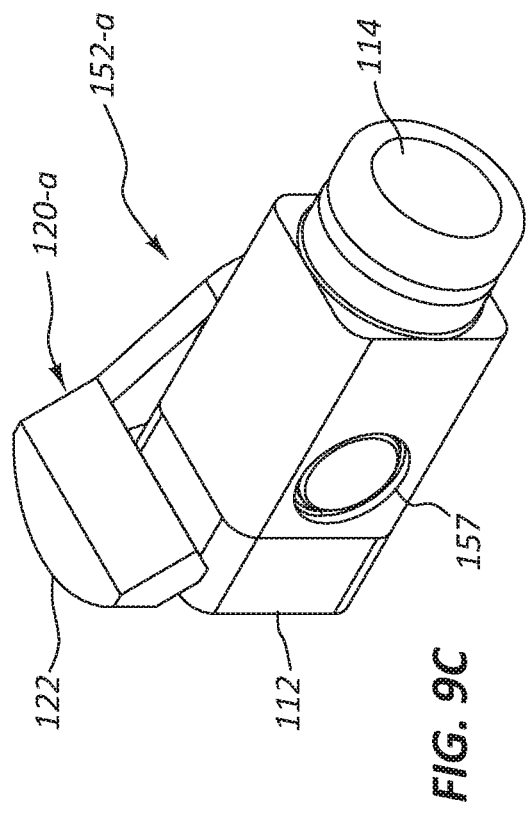

Referring now to FIGS. 9A-9D, a portion of a valve assembly 104 is shown according to an embodiment of the present disclosure. FIGS. 9A and 9B show the valve plug 120-a placed in an "ON" position, while FIGS. 9C and 9D show the valve plug 120-a rotated to an "OFF" position. In the "OFF" position, the through-passage 130 is positioned relative to the flow path between inlet and outlet ends of body portion 152-a of valve body 110 so as to impede fluid flow through the valve body 110.

Figure 10A:
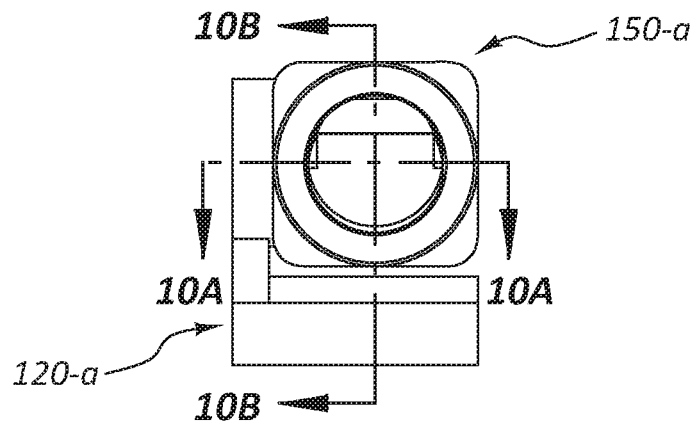
FIGS. 10A-C show the portion of a valve assembly shown in FIGS. 9A and 9B with the valve member an open position.
Figure 10B:
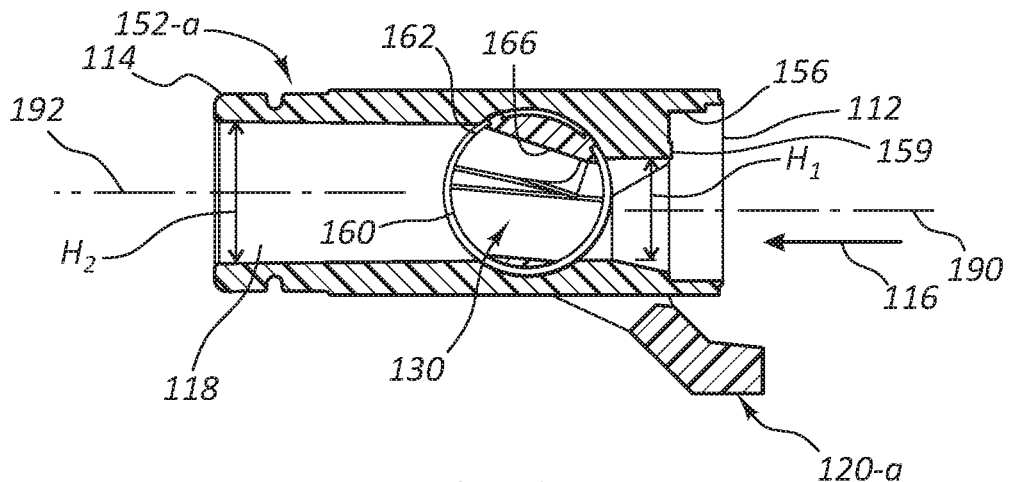
Figure 10C:
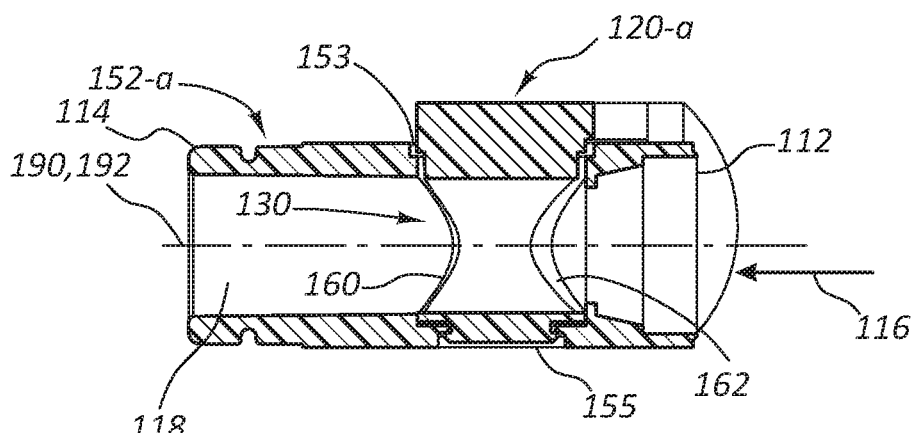

As illustrate in FIGS. 10B and 10C, the through-passage 130 of valve plug 120 may be configured to exhibit a varied cross-sectional area along a length of its flow path. The through-passage 130 may be defined in part by a ramp surface 166. In some embodiments, such a construction may result in offset centerlines 190, 192 of the flow path passing through the valve body 110. For example, as seen in FIG. 10B, the height H1 of the opening leading into the through-passage 130 may be substantially smaller than the height H2 of the opening leading out of the through-passage 130. The centerlines 190, 192 may be concentric and positioned about a common plane, as seen in the top view of FIG. 9B. Generally, the flow path through the body portion 152-a has a centerline 190 leading into the through-passage 130 which is offset from the centerline 192 of a flow path leaving the through-passage 130.

In addition to providing a short throw-length for rotating the valve plug 120 between ON and OFF, the offset arrangement shown in FIG. 10B may also provide the valve body 110 with one or more valve retention features 159 that may be used to abut and clamp a peripheral portion of a resilient member 142 of a backflow prevention device 140 such as has been previously discussed.

Figure 11A:
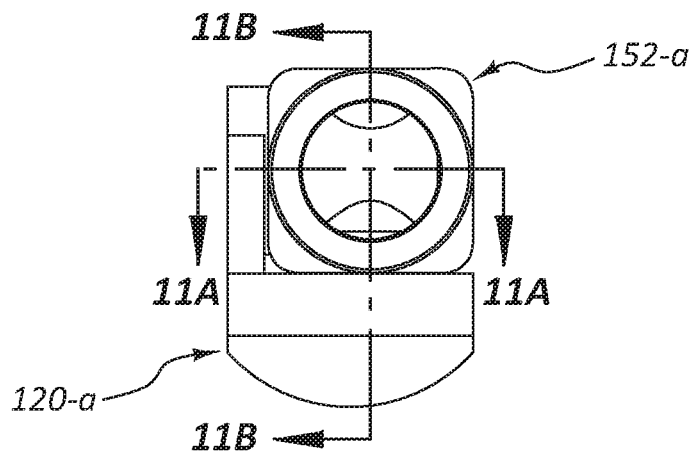
FIGS. 11A-C show the portion of a valve assembly shown in FIGS. 9A and 9B with the valve member in a closed position.
Figure 11B:
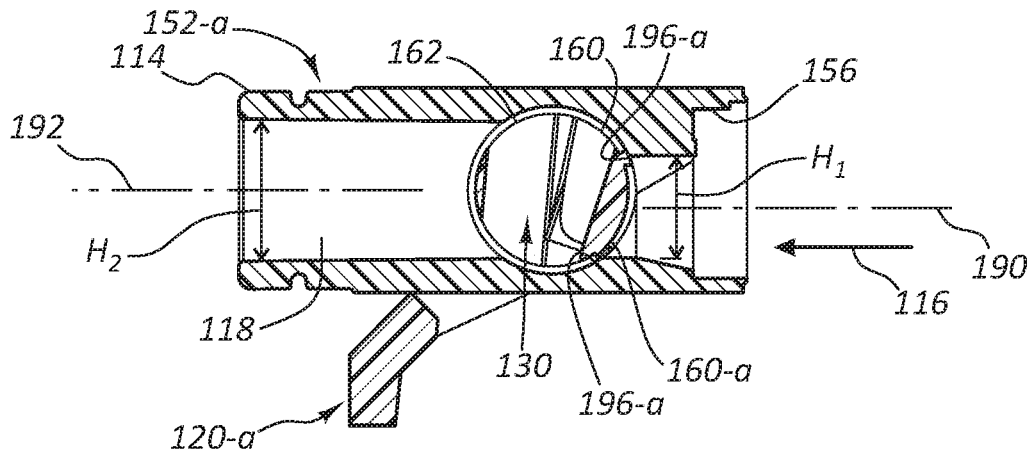
Figure 11C:
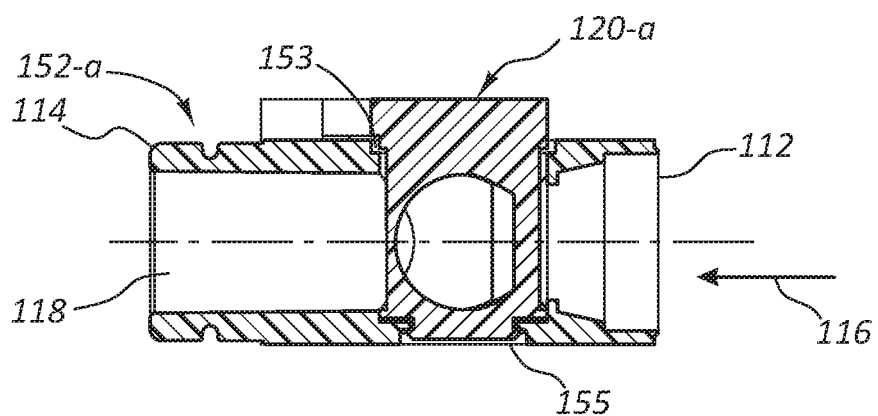

FIGS. 11A-11C show the portion of valve assembly 104 shown in FIGS. 9C and 9D with the valve plug 120-a rotated into a closed or "OFF" position. In the closed position, a front sealing surface 160-a is arranged at a distal or front side (e.g., an entrance side) of the valve plug 120-a to contact a sealing surface 194 of the valve body portion 152-a at the entrance side of the valve plug 120-a to form a seal therebetween. The embodiment of FIGS. 10A-11C may also provide a seal between the valve plug 120-a and the valve body portion 152-A along a rotation axis of the valve plug 120-a.

Figure 12A:
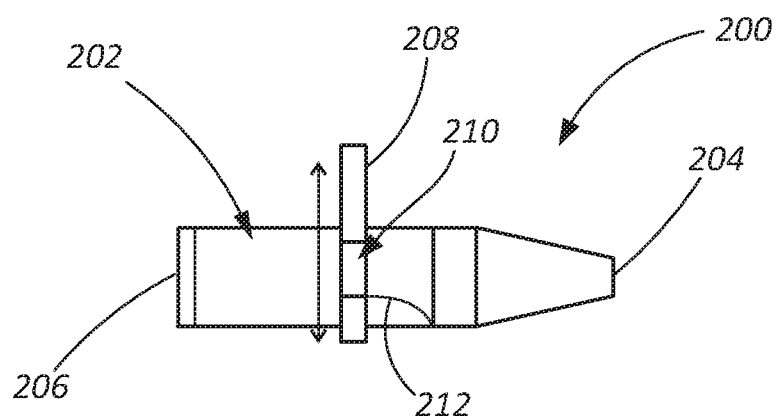
FIGS. 12A-12C are side and top views of a valve device according to an embodiment of the present disclosure.
Figure 12B:
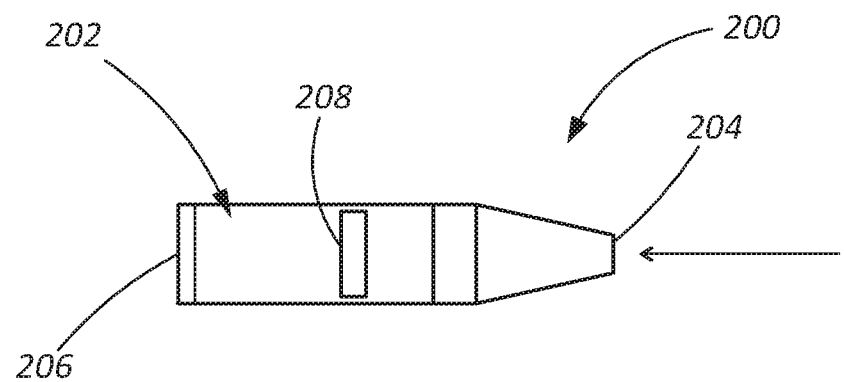
Figure 12C:
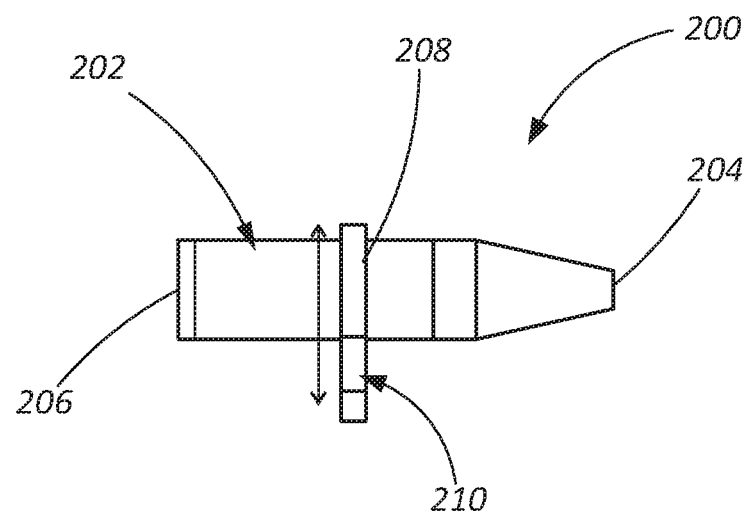

Referring to FIGS. 12A-12C, another embodiment of a valve assembly 200 is shown. FIGS. 12A and 12C are side views of a the valve assembly 200 while FIG. 1wB is a top view of the valve assembly 200. The valve assembly 200 includes a valve body 202 having an inlet 204 and an outlet 206, and a valve gate 208 configured to slide relative to the valve body in a direction that is at an angle (e.g., perpendicular to) the flow path between the inlet 204 and the outlet 206. As seen in FIG. 12B, the gate 208 may be configured as a rectangular plate member. The gate 208 may slide between an ON position, wherein a through passage 210 is aligned with the flow path of the valve body 202 (see FIG. 12A) and an OFF position wherein the through-passage is not aligned with the flow path and, instead, fluid flow is blocked by the gate 208 from flowing between the inlet 204 and the outlet 206. In some embodiments, the valve assembly 200 may also include a backflow prevention device, such as a one way backflow prevention member 212 as has been discussed above. As with other embodiments, while FIGS. 12A and 12C show a backflow prevention member 212 positioned upstream of the gate 208, it may also be positioned downstream of the gate, or a plurality of backflow prevention members 212 may be used on either or both sides of the gate 208.

Figure 13A:
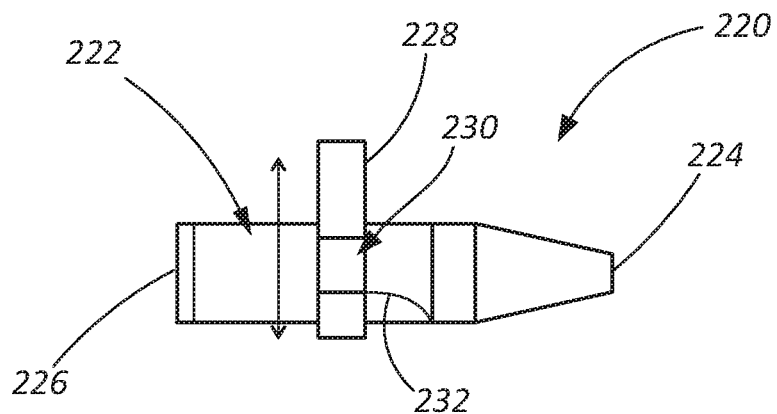
FIG. 13A-13C are side and top views of a valve device according to an embodiment of the present disclosure.
Figure 13B:
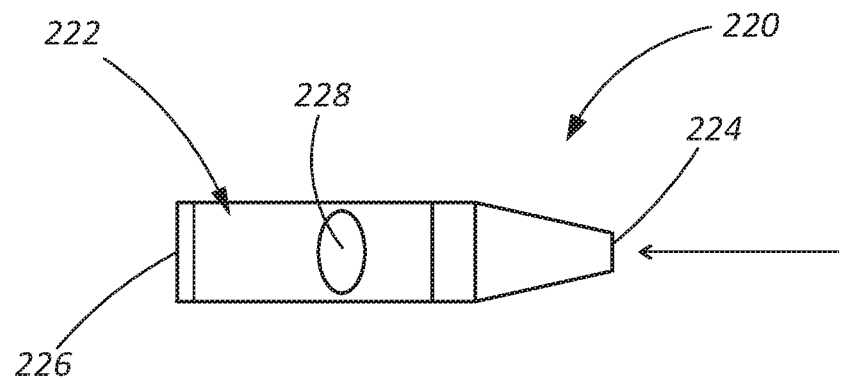
Figure 13C:
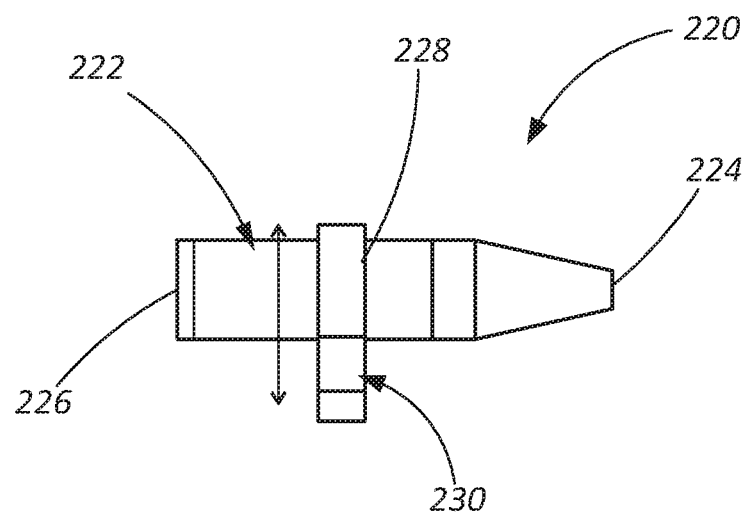

Referring to FIGS. 13A-13C, another embodiment of a valve assembly 220 is shown. FIGS. 13A and 13C are side views of a the valve assembly 220 while FIG. 13B is a top view of the valve assembly 220. The valve assembly 220 includes a valve body 222 having an inlet 224 and an outlet 226, and a slidable valve plug 228 configured to slide relative to the valve body 222 in a direction that is at an angle (e.g., perpendicular to) the flow path between the inlet 224 and the outlet 226. As seen in FIG. 13B, the plug 228 may be configured as a cylindrical member. The plug 228 may slide between an ON position, wherein a through-passage 230 is aligned with the flow path of the valve body 222 (see FIG. 13A) and an OFF position wherein the through-passage 230 is not aligned with the flow path and, instead, the plug 228 blocks fluid from flowing between the inlet 224 and the outlet 226. In some embodiments, the valve assembly 220 may also include a backflow prevention device, such as a one way backflow prevention member 232 as has been discussed above. As with other embodiments, while FIGS. 13A and 13C show a backflow prevention member 232 positioned upstream of the plug 228, it may also be positioned downstream of the plug 228. In other embodiments, a plurality of backflow prevention members 232 may be used on either or both sides of the plug 228.

While the invention may be susceptible to various modifications and alternative forms, specific embodiments have been shown by way of example in the drawings and have been described in detail herein. For example, components, features or aspects of one described embodiment may be combined with components, features or aspects of other embodiments without limitation. However, it should be understood that the invention is not intended to be limited to the particular forms disclosed. Rather, the invention includes all modifications, equivalents, and alternatives falling within the spirit and scope of the invention as defined by the following appended claims.

What is claimed is:

1. A dental suction system, comprising:
   an ejector tube; and
   a valve body having an inlet configured for connection with the ejector tube, an outlet configured for direct connection with a vacuum hose, and a fluid flow path extending between the inlet and the outlet;
   a valve plug positioned at least partially within the valve body, the valve plug including a through-passage, the valve plug being rotatable relative to the valve body to selectively alter a flow of fluid along the fluid flow path, wherein the fluid flow path exhibits a varied cross-sectional area along a length of the fluid flow path, wherein the through-passage includes a first opening on a first side of the valve plug, and a second opening on a second side of the valve plug; and
   a ramped surface positioned in the fluid flow path of the valve body located outside of the valve plug between a proximal end of the valve plug and the outlet of the valve body providing a transition to the outlet of the valve body; wherein an outlet opening of the outlet has a larger cross-sectional area than a cross-sectional area of the through-passage in the valve plug.

2. The valve assembly of claim 1, wherein, when the through-passage is aligned with the fluid flow path to permit fluid flow through the valve body, the fluid flow path includes a first portion having a first centerline and a second portion having a second centerline, wherein the first centerline is offset from the second centerline.

3. The valve assembly of claim 1, wherein the first opening exhibits a semicircular geometry, and wherein the second opening exhibits a semicircular geometry.

4. The valve assembly of claim 1, wherein the valve plug forms a seal with the valve body along the proximal e n d of the valve plug when the valve plug is in a closed position.

5. The valve assembly of claim 1, further comprising at least one backflow prevention device disposed in the fluid flow path.

6. The valve assembly of claim 5, wherein the at least one backflow prevention device is positioned between the valve plug and the inlet of the valve body.

7. The valve assembly of claim 5, wherein the at least one backflow prevention device is positioned between the valve plug and the outlet of the valve body.

8. The valve assembly of claim 5, wherein the at least one backflow prevention device comprises a flexible and resilient material, and is movable relative to the valve body to control fluid flow through the fluid flow path independent of operation of the valve plug.

9. The dental suction system of claim 1, further comprising the vacuum hose.

10. A valve assembly for a dental suction system, comprising:
    an ejector tube;
    a valve body having an inlet configured for connection with the ejector tube, an outlet configured for direct connection with a vacuum hose of the dental suction system, and a fluid flow path extending between the inlet and the outlet;
    a valve plug positioned at least partially within the valve body, the valve plug including a through-passage, the valve plug being displaceable relative to the valve body to selectively alter a flow of fluid along the fluid flow path; and
    a backflow prevention device disposed in the fluid flow path between the valve plug and the inlet of the valve body or between the valve plug and the outlet of the valve body, the backflow prevention device being movable between open and closed positions to control fluid flow through the fluid flow path independent of operation of the valve plug; and
    a ramped surface positioned in the fluid flow path, wherein the ramped surface is not located in the through-passage of the valve body; wherein an outlet opening of the outlet has a larger cross-sectional area than a cross-sectional area of the through-passage in the valve plug.

11. The valve assembly of claim 10, wherein the backflow prevention device includes a resilient, flexible member having a peripheral portion fixed relative to the valve body.

12. The valve assembly of claim 10, wherein the fluid flow path is configured such that the fluid flow path includes a first portion having a first centerline distal of the valve plug and a second portion having a second centerline proximal of the valve plug, the first centerline being offset from the second centerline.

13. The valve assembly of claim 10, wherein the valve plug is rotatable between open and closed positions.

14. The valve assembly of claim 10, wherein the valve plug sealingly engages the valve body when the valve plug is in a closed position to block fluid flow through the fluid flow path.

15. A dental suction system, comprising:
    an ejector tube; and
    a valve assembly comprising:
    a first valve body having a first inlet configured for connection with the ejector tube, a first outlet, and a first fluid flow path extending between the first inlet and the first outlet;
    a second valve body having a second inlet, a second outlet configured for direct connection with a vacuum hose, and a second fluid flow path extending between the second inlet and the second outlet;
    a backflow prevention device captured between the first and second valve bodies, the backflow prevention device being movable to control fluid flow along at least one of the first and second fluid flow paths;
    a valve plug positioned at least partially within the second valve body, the valve plug including a through-passage, the valve plug being displaceable relative to the second valve body to selectively alter a flow of fluid along at least one of the first and second fluid flow paths; and a ramped surface positioned in the second flow path between the valve plug and the second outlet of the second valve body; wherein an outlet opening of the second outlet has a larger cross-sectional area than a cross-sectional area of the through-passage in the valve plug.

16. The valve assembly of claim 15, wherein the first fluid flow path includes a first portion having a first centerline distal of the valve plug and the second fluid flow path includes a second portion having a second centerline proximal of the valve plug, the first centerline being offset from the second centerline.

17. The valve assembly of claim 15, wherein the backflow prevention device is positioned between the valve plug and the first inlet.

18. The valve assembly of claim 15, wherein the backflow prevention device is positioned between the valve plug and the first outlet.

19. The valve assembly of claim 15, wherein at least one of the first and second valve bodies includes an alignment feature configured to align the first valve body relative to the second valve body in a predetermined rotated position.

* * * * *